(12) United States Patent
Koo

(10) Patent No.: US 10,000,436 B2
(45) Date of Patent: Jun. 19, 2018

(54) METHOD FOR PREPARING ORGANIC VAPOR-PHASE DEHYDRATION FEEDSTOCK

(71) Applicant: SK Innovation Co., Ltd., Seoul (KR)

(72) Inventor: Min Su Koo, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days. days.

(21) Appl. No.: 15/380,222

(22) Filed: Dec. 15, 2016

(65) Prior Publication Data

US 2017/0197901 A1 Jul. 13, 2017

(30) Foreign Application Priority Data

Jan. 8, 2016 (KR) .................. 10-2016-0002684

(51) Int. Cl.
*C07B 35/00* (2006.01)
*C07C 51/377* (2006.01)
*C07C 51/43* (2006.01)

(52) U.S. Cl.
CPC ............ *C07C 51/377* (2013.01); *C07C 51/43* (2013.01)

(58) Field of Classification Search
CPC ..... C07C 51/377; C07C 51/43; B01D 53/005; B03C 3/00; C12P 7/02; C12P 7/52; C12P 7/56
See application file for complete search history.

(56) References Cited

U.S. PATENT DOCUMENTS

| 5,420,304 | A | * | 5/1995 | Verser ................. C07C 51/48 549/274 |
| 6,489,508 | B1 | | 12/2002 | Van Gansbeghe et al. |
| 6,538,164 | B1 | * | 3/2003 | Gallagher ............... B01D 1/16 209/133 |
| 8,597,918 | B2 | | 12/2013 | Clark et al. |
| 2001/0006104 | A1 | * | 7/2001 | Okazaki ............. B01J 19/0013 165/164 |
| 2013/0071893 | A1 | * | 3/2013 | Lynch .................... A61L 15/24 435/136 |
| 2013/0122145 | A1 | * | 5/2013 | Lewandowski ........ A23C 9/127 426/41 |
| 2017/0015616 | A1 | | 1/2017 | Gwak et al. |

FOREIGN PATENT DOCUMENTS

KR 20150115533 A1 10/2015
WO 9855442 A1 12/1998

* cited by examiner

*Primary Examiner* — Yevgeny Valenrod
*Assistant Examiner* — Blaine G Doletski
(74) *Attorney, Agent, or Firm* — The Webb Law Firm

(57) ABSTRACT

The present invention relates to a method including: directly heating a fermentation broth to remove impurities, thereby preparing an organic vapor-phase dehydration feedstock; and continuously subjecting the organic vapor-phase dehydration feedstock to a vapor-phase dehydration reaction. According to the present invention, impurities in a fermentation broth, which have been removed by a multi-step process in the prior art, can be completely removed in a single-step process, and thus the time, cost and energy required for a process for preparing an organic vapor-phase dehydration feedstock from the fermentation broth can be effectively reduced, and the process for preparing the organic vapor-phase dehydration feedstock and a vapor-phase dehydration reaction can be continuously performed in an effective manner.

14 Claims, 1 Drawing Sheet

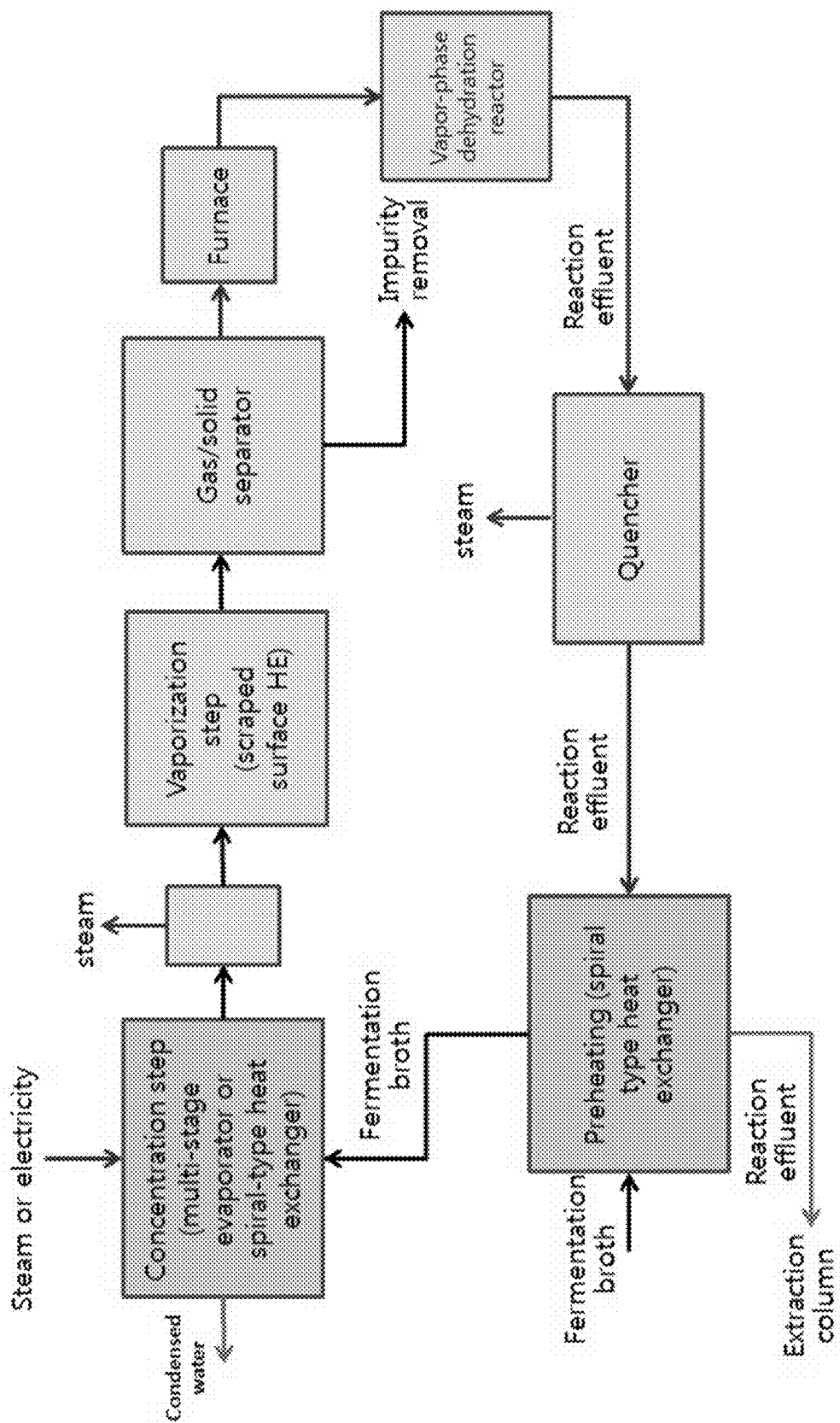

METHOD FOR PREPARING ORGANIC VAPOR-PHASE DEHYDRATION FEEDSTOCK

CROSS-REFERENCE TO RELATED APPLICATION

This application claims priority to Korean Patent Application No. 10-2016-0002684 filed Jan. 8, 2016, the disclosure of which is hereby incorporated in its entirety by reference.

TECHNICAL FIELD

The present invention relates to a method for preparing an organic vapor-phase dehydration feedstock, and more particularly to a method for preparing an organic vapor-phase dehydration feedstock, which comprises directly heating a fermentation broth to remove impurities.

BACKGROUND ART

Along with an increase in the price of petroleum-based hydrocarbons due to a decrease in the petroleum-based hydrocarbon supply, the development and improvement of industrial microbial systems for production of chemical compounds and fuels has been of increasing interest. Such industrial microbial systems can completely or partially replace the use of petroleum-based hydrocarbons for production of specific chemical compounds.

Through such systems, many chemical compounds, including antibiotics, anti-malarial drugs, high-quality chemical compounds and fuels such as ethanol, are produced.

Despite strong interest in increasing the yield and production of specific chemical products, efforts are required to develop methods for producing desired chemical products from fermentative microbial cells by feasible fermentation processes and converting the chemical compounds into other compounds.

Fermentation broths produced by biological processes contain not only chemical products, but also microorganisms producing the chemical products, and various organic impurities produced by the metabolic activity of such microorganisms. If organic impurities remain in a chemical product separated from a fermentation broth, these impurities will interfere with a subsequent reaction process for converting the chemical product to another compound. For this reason, it is required to remove these organic impurities to the greatest possible extent.

As methods for solving this problem, International Patent Publication No. WO1998-055442 discloses a method of obtaining a chemical product by subjecting a fermentation product to a pretreatment step, a concentration step and a distillation step. U.S. Pat. No. 8,597,918 discloses a method of obtaining a high-purity chemical product by separating a liquid fraction from a fermentation broth, removing water from the liquid fraction, and removing salts from the liquid fraction, followed by distillation. The above-described methods are methods of removing impurities by centrifugation, ultrafiltration, nanofiltration, ion exchange and salt removal, and thus entail problems in that the impurity removal process consisting of several steps is time-consuming and costly and in that chromatography for ion exchange is difficult to apply to commercial processes and the use of ion exchange resin causes environmental pollution problems.

As a method for solving such problems, Korean Unexamined Patent Application Publication No. 2015-0115533 discloses a method of obtaining a high-purity purified chemical product by subjecting a fermentation broth to a concentration step, a decarbonization step, a pH adjustment and a recovery step using a distillation column. However, this method has problems in that large amounts of acidic solution and basic solution are used which cause environmental pollution and in that metal salts are not efficiently removed.

Accordingly, the present inventors have made extensive efforts to effectively prepare an organic vapor-phase dehydration feedstock from a fermentation broth, and as a result, have found that a gaseous organic vapor-phase dehydration feedstock can be separated from a fermentation broth by direct heating and concentration of the fermentation broth without a separate impurity removal process and can be continuously subjected to a vapor-phase dehydration reaction, thereby completing the present invention.

DISCLOSURE OF INVENTION

It is an object of the present invention to provide a method for preparing an organic vapor-phase dehydration feedstock, which enables impurities to be removed from a fermentation broth in a simple manner so as to reduce operation costs and process energy, and a method of continuously converting the prepared organic vapor-phase dehydration feedstock to another compound by vapor-phase dehydration.

To achieve the above object, the present invention provides a method of preparing an organic vapor-phase dehydration feedstock, comprising the steps of: (a) concentrating a fermentation broth containing a low concentration of an organic compound by direct heating at a temperature of 100° C. or lower under a vacuum; (b) heating a concentrated fermentation broth of the step of (a) to a temperature of 100 to 250° C. thereby vaporizing the remaining water and the organic compound; (c) separating a vaporized organic compound of the step of (b) from impurities present in the fermentation broth; and (d) heating a gas separated in the step of (c) to a vapor-phase dehydration reaction temperature.

The present invention also provides a method of converting an organic compound by vapor-phase dehydration comprising: heating the organic vapor-phase dehydration feedstock prepared by the previous method to a reaction temperature; and carrying out a vapor-phase dehydration reaction.

BRIEF DESCRIPTION OF THE DRAWINGS

The FIGURE is a process diagram showing a method for preparation of an organic vapor-phase dehydration feedstock according to the present invention and a method of converting the organic vapor-phase dehydration feedstock by vapor-phase dehydration reaction.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods, which will be described below, are those well-known and commonly employed in the art.

A chemical product produced by a microbial fermentation process that is an industrial microbial system can be converted to another compound by a reaction process. However, a fermentation broth resulting from a microbial fermentation process contains, in addition to a chemical product, many impurities, including microorganisms, proteins, anions and cations, which interfere with a process of converting the chemical product to another compound.

In the present invention, a fermentation broth was directly heated in order to confirm that the fermentation broth could be easily separated into impurities and an organic vapor-phase dehydration feedstock. Furthermore, in the present invention, the prepared organic vapor-phase dehydration feedstock was subjected to a vapor-phase dehydration reaction in order to confirm that the organic feedstock could be continuously converted to another compound.

In an example of the present invention, a fermentation broth was directly heated and concentrated to agglomerate impurities, and resulting organic vapor-phase dehydration feedstock was vaporized. As a result, it could be seen that the impurities in the fermentation broth agglomerated and were easily separated from the vaporized organic vapor-phase dehydration feedstock.

Therefore, in one aspect, the present invention is directed to a method of preparing an organic vapor-phase dehydration feedstock, comprising the steps of: (a) concentrating a fermentation broth containing a low concentration of an organic compound by direct heating at a temperature of 100° C. or lower under a vacuum; (b) heating a concentrated fermentation broth of the step of (a) to a temperature of 100 to 250° C. thereby vaporizing the remaining water and the organic compound; (c) separating a vaporized organic compound of the step of (b) from impurities present in the fermentation broth; and (d) heating a gas separated in the step of (c) to a vapor-phase dehydration reaction temperature.

In the present invention, the organic compound-containing fermentation broth of step of (a) may contain an organic compound produced by microbial fermentation. Furthermore, the organic compound produced by microbial fermentation may have a boiling point higher than that of water and, at the same time, may be converted to another compound by a vapor-phase dehydration reaction. The fermentation broth may contain an organic compound selected from the group consisting of 3-hydroxypropionic acid, lactic acid, alcohols having 4 or more carbon atoms, and cyclic alcohols, but is not limited thereto. 3-hydroxypropionic acid, lactic acid, alcohols having 4 or more carbon atoms, and cyclic alcohols have a boiling point higher than that of water, and are converted into an unsaturated hydrocarbon compound by a vapor-phase dehydration reaction. Examples of alcohols having 4 or more carbon atoms include buthanol, penthanol, and hexanol. An example of cyclic alcohols includes 2-methyl-1-cyclohexane, but is not limited thereto.

In the present invention, step of (a) may comprise directly heating the organic compound-containing fermentation broth to a temperature of 38 to 110° C. under a vacuum of 50-750 Torr to concentrate the fermentation broth. At high temperature, cations present in the fermentation broth will act as a catalyst to cause the polymerization of the organic compound contained in the fermentation broth to cause fouling of a heat exchange and to reduce the recovery of the organic compound. For this reason, step of (a) is preferably performed at a reduced temperature under a vacuum of 50-750 Torr so that only water can be evaporated.

When the fermentation broth is heated to a temperature of 38 to 100° C. under a vacuum of 50-750 Torr, the fermentation broth can be concentrated so that a low concentration of the organic compound in the fermentation broth reaches a high concentration. The concentration of the organic compound in the fermentation broth before step of (a) (concentrating step) may be 1-30 wt %, and the concentration of the organic compound in the fermentation broth after step of (a) (concentrating step) may be 30-80 wt %. Because a large amount of water is used to promote the fermentation of microorganisms in a microbial fermentation process for producing the organic compound, the concentration of the organic compound in the fermentation broth after the microbial fermentation process may be as low as about 1-30 wt %. Step of (a) is a concentration process of evaporating water from the fermentation broth. In this step, the concentration of the organic compound in the fermentation broth can be increased to 30-80 wt % by evaporation of water.

The temperature in step of (a) may be reduced as the vacuum level increases. The temperature at which water is vaporized decreases as the vacuum level increases. For this reason, when the vacuum level is high, the heating temperature of the fermentation broth is preferably decreased, and when the vacuum level is low, the heating temperature of the fermentation broth is preferably increased.

If water is removed by heating of the fermentation broth in step of (a), impurities will easily agglomerate with one another in step of (b) to form easy-to-remove solid agglomerates, and thus energy required for removal of impurities will be effectively reduced.

In the present invention, the concentration of the fermentation broth in step of (a) may be performed using a spiral-type heat exchanger or a multi-stage evaporator, but is not limited thereto. The spiral-type heat exchanger is a heat exchanger having a vortex flow channel formed between two flat plates. Even when slurry is generated, it can be transported along the vortex flow channel so as to minimize fouling of the heat exchanger, and thus the spiral-type heat exchanger is used in processes in which slurry can be generated. The multi-stage evaporator can increase the surface area of an introduced fluid under a vacuum, can easily evaporate light compounds from a fluid, and is an exchanger composed of multiple stages in order to increase the amount of evaporation. It is an apparatus suitable for concentrating a fluid without loss of heavy compounds in the fluid.

In the present invention, as shown in the FIGURE, step of (a) may further comprise, before the concentrating step, a preheating step. The preheating step is a step of applying a certain amount of heat to the fermentation broth before direct heating of the fermentation broth in step of (a). In the preheating step, the fermentation broth may be preheated by heat contained in a vapor-phase dehydration reaction effluent to reduce the amount of heat required for an evaporator and to prevent the heat of the vapor-phase dehydration reaction effluent from being lost by cooling.

In the present invention, step of (b) may comprise heating the concentrated fermentation broth of step of (a) to a temperature of 100 to 250° C. to vaporize the organic compound. The heating temperature in step of (b) varies depending on the kind of organic compound, but may generally be between 100° C. and 250° C. under a vacuum of 40-80 Torr. If the heating temperature is lower than 100° C., an organic compound having a boiling point higher than that of water will not be vaporized, and if the heating temperature is higher than 250° C., impurities will be decomposed and vaporized, or the organic compound will be polymerized, and thus lost. In addition, when the concentrated fermentation broth is heated to a temperature between 100° C. and 250° C., the organic compound and water are vaporized, and impurities are not vaporized, indicating that the impurities and the vaporized organic compound and water can be easily separated from each other. Thus, the heating in step of (b) is preferably performed to a temperature between 100° C. and 250° C.

In step of (b), the fermentation broth may be directly heated to agglomerate and solidified impurities. When the concentrated fermentation broth is heated to a temperature between 100° C. and 250° C. under a vacuum of 40-80 Torr, the organic compound and the remaining water is vaporized to provide an organic vapor-phase dehydration feedstock, and agglomerated solid impurities in the concentrated fermentation broth are not vaporized, indicating that the organic compound and the impurities are easily separated from each other. If step of (b) is performed under atmospheric pressure or increased pressure rather than a vacuum, the yield of the resulting organic vapor-phase dehydration feedstock can be reduced due to the reaction of the organic compound in the fermentation broth. For this reason, step of (b) is preferably performed under a vacuum.

In the present invention, step of (b) may be performed by directly heating the concentrated fermentation broth using a scraped surface heat exchanger, but is not limited thereto. The scraped surface heat exchanger is a heat exchanger equipped with a surface scraper that prevents the heat transfer effect from being reduced by attachment of a highly viscous fluid or slurry to the heat transfer surface. This heat exchanger is preferably used to heat a fermentation broth containing a high concentration of a highly viscous organic compound to thereby vaporize the organic compound.

In the present invention, step of (c) may comprise separating the vaporized organic compound of step of (b) and the remaining water by a solid/gas separator or an electrostatic precipitator. In step of (b), impurities are agglomerated to form solids, and the organic compound and the remaining water are vaporized to form a gaseous material. Thus, the organic compound and the remaining water are preferably separated from the impurities by a solid/gas separator or an electrostatic precipitator that uses an electrostatic force by anions or cations.

In the present invention, step of (d) may comprise heating the separated organic compound and remaining water of step of (c) to a vapor-phase dehydration temperature to thereby prepare an organic vapor-phase dehydration feedstock. When the separated organic compound and remaining water of step of (c) are heated to a vapor-phase dehydration temperature between 300° C. and 500° C., the separated organic compound may become an organic vapor-phase dehydration feedstock that is to be converted to another compound by a vapor-phase dehydration reaction. In step of (d), the temperature of the gaseous organic compound may be increased using a furnace.

In the present invention, the method for preparing the organic vapor-phase dehydration feedstock makes it possible to perform impurity removal and organic compound vaporization in a single-step process by directly heating the fermentation broth, unlike a conventional method in which an organic compound is vaporized after impurities in a fermentation broth are removed by several steps. The method for preparing the organic vapor-phase dehydration feedstock according to the present invention is a method of removing impurities while vaporizing the organic compound, and does not require additional energy or costs for impurity removal, and thus may have the effect of reducing process energy and operation costs. In addition, the method according to the present invention reduces costs and causes no environmental pollution problems, because an adsorbent, ion exchange resin, a filter or a chemical agent for regeneration is not used for impurity removal.

In another example of the present invention, the prepared organic vapor-phase dehydration feedstock was subjected to a vapor-phase dehydration reaction in a vapor-phase dehydration reactor. As a result, it could be seen that the prepared organic vapor-phase dehydration feedstock was converted to an unsaturated hydrocarbon compound by the vapor-phase dehydration reaction.

Therefore, in another aspect, the present invention is directed to a method of converting an organic compound by vapor-phase dehydration comprising: heating the organic vapor-phase dehydration feedstock prepared by the previous method to a reaction temperature; and carrying out a vapor-phase dehydration reaction.

An organic vapor-phase dehydration feedstock prepared according to an embodiment of the present invention may be heated a vapor-phase dehydration reaction temperature under a vacuum of 10-400 Torr. The vapor-phase dehydration reaction temperature varies depending on the kind of organic vapor-phase dehydration feedstock, but may generally range from 200° C. to 1000° C., preferably 300 to 500° C., under a vacuum of 10-400 Torr. If the vapor-phase dehydration reaction takes place under atmospheric pressure or increased pressure rather than a vacuum, the vapor-phase dehydration reaction will occur reversibly to reduce the yield of conversion. For this reason, the vapor-phase dehydration reaction is preferably performed under a vacuum.

In the present invention, the organic vapor-phase dehydration feedstock may be subjected to a vapor-phase dehydration reaction in a vapor-phase dehydration reactor so as to be converted to an unsaturated hydrocarbon compound. Each of the organic vapor-phase dehydration feedstocks prepared in Example 1 may be converted to another compound by the vapor-phase dehydration reaction as shown in Table 1 below.

TABLE 1

| Organic compounds | Compounds converted after vapor-phase dehydration reaction |
|---|---|
| 3-hydroxypropionic acid | Acrylic acid |
| lactic acid | Acrylic acid |
| Linear alcohols (e.g., buthanol) | Alkenes (e.g., butene) |
| Cyclic alcohols (e.g., 2-methyl-1-cyclohexane) | Cycloalkenes (e.g., 1-methylcyclohexene) |

Each of the compounds converted by the vapor-phase dehydration reaction includes an unsaturated hydrocarbon compound, and thus is used to manufacture various kinds of polymers by a polymerization reaction.

As shown in the FIGURE, the method of vapor-phase dehydration of the organic vapor-phase dehydration feedstock according to the present invention may further comprise, after the vapor-phase dehydration reaction, a quenching step of cooling the reaction effluent while removing water by adding to the reaction effluent a solvent capable of removing the remaining water without reacting with the reaction effluent, and a step of preheating the fermentation broth by the remaining heat of the reaction effluent.

In the present invention, the quenching step is a step of cooling the reaction effluent and removing the remaining water. To cool the reaction effluent, a solvent may be used at a temperature of 20 to 80° C., preferably 30 to 50° C. The solvent is capable of removing the remaining water without reacting with the reaction effluent, and examples thereof include, but are not limited to, toluene, p-xylene, o-xylene, m-xylene, butyl acetate, and ethyl acetate.

In the present invention, the preheating step may be a step in which a fermentation broth to be used for preparation of the organic vapor-phase dehydration feedstock is preheated by the remaining heat of the reaction effluent. The preheating step is a step of reducing the temperature of the reaction effluent after the high-temperature vapor-phase dehydration reaction and preheating the fermentation broth, and can reduce heat loss which can occur in cooling with cooling water. In addition, the preheating step can reduce the amount of heat required for an evaporator that concentrates the fermentation broth.

In the present invention, the vapor-phase dehydration reaction of the organic compound may be performed continuously with the process for preparation of the organic vapor-phase dehydration feedstock. The vapor-phase dehydration feedstock is a gaseous organic compound that may be subjected to a vapor-phase dehydration reaction directly after preparation thereof.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

1-1: Preparation of 3-Hydroxypropionic Acid as Vapor-Phase Dehydration Feedstock A fermentation broth containing 3-hydroxypropionic acid produced by microbial fermentation was prepared. The concentration of 3-hydroxypropionic acid produced by microbial fermentation was 10 wt %. The fermentation broth was concentrated by heating to 90° C. by a spiral-type heat exchanger under a vacuum of 500 Torr. Concentration of the fermentation broth by heating was performed until the concentration of 3-hydroxypropionic acid in the fermentation broth reached 60 wt %. The concentrated fermentation broth having a 3-hydroxypropionic acid concentration of 60 wt % was heated to 180° C. in a scraped surface heat exchanger under a vacuum of 50 Torr. In the scraped surface heat exchanger, the fermentation broth was vaporized, and the remaining material was solidified. The vaporized material and the solidified fermentation broth were transferred into a solid/gas separator in which the vaporized material was separated from the solidified material. Then, the vaporized material was transferred into a furnace. The material transferred into the furnace was heated to 350° C., and then analyzed.

As a result, the vaporized material was composed of 3-hydroxypropionic acid and water. In addition, it could be seen that, when the fermentation broth was heated by the spiral-type heat exchanger and the scraped surface heat exchanger, the fermentation broth was concentrated while impurities agglomerated.

2-1: Preparation of 3-Hydroxypropionic Acid as Vapor-Phase Dehydration Feedstock A fermentation broth containing 3-hydroxypropionic acid produced by microbial fermentation was prepared. The concentration of 3-hydroxypropionic acid produced by microbial fermentation was 10 wt %. The fermentation broth preheated to 70° C. was concentrated by heating to 80° C. by a multi-stage evaporator under a vacuum of 350 Torr. Concentration of the fermentation broth by heating was performed until the concentration of 3-hydroxypropionic acid in the fermentation broth reached 70 wt %. The concentrated fermentation broth having a 3-hydroxypropionic acid concentration of 70 wt % was heated to 200° C. in a scraped surface heat exchanger under a vacuum of 70 Torr. In the scraped surface heat exchanger, the fermentation broth was vaporized, and the remaining material was solidified. The vaporized material and the solidified fermentation broth were transferred into a solid/gas separator in which the vaporized material was separated from the solidified material. Then, the vaporized material was transferred into a furnace. The material transferred into the furnace was heated to 350° C., and then analyzed.

As a result, the vaporized material was composed of 3-hydroxypropionic acid and water. In addition, it could be seen that, when the fermentation broth was heated by the spiral-type heat exchanger, the multi-stage evaporator, and the scraped surface heat exchanger, the fermentation broth was concentrated while impurities agglomerated.

Example 2

2-1: Vapor-Phase Dehydration Reaction of 3-Hydroxypropionic Acid

The vapor-phase dehydration feedstock prepared in Examples 1-1 and 1-2 was transferred into a vapor-phase dehydration reactor in which the feedstock was heated to 450° C. under a vacuum of 300 Torr. The vapor-phase dehydration feedstock was subjected to a vapor-phase dehydration reaction while it was heated under a vacuum. To the reaction effluent obtained by the vapor-phase dehydration reaction of the feedstock, toluene at 40° C. was added to cool the reaction effluent and remove a portion of the remaining water. The reaction effluent obtained after cooling and the removal of the remaining water was analyzed.

As a result, it could be seen that acrylic acid was produced by the vapor-phase dehydration reaction of 3-hydroxypropionic acid.

INDUSTRIAL APPLICABILITY

According to the present invention, impurities in a fermentation broth, which have been removed by a multi-step process in the prior art, can be completely removed in a single-step process, and thus the time, cost and energy required for a process for preparing an organic vapor-phase dehydration feedstock from the fermentation broth can be effectively reduced, and the process for preparing the organic vapor-phase dehydration feedstock and a vapor-phase dehydration reaction can be continuously performed in an effective manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of preparing an organic vapor-phase dehydration feedstock, comprising the steps of:

(a) concentrating a fermentation broth containing a low concentration of an organic compound by direct heating at a temperature of 100° C. or lower under a vacuum thereby evaporating water only;

(b) heating a concentrated fermentation broth of the step of (a) to a temperature of 100 to 250° C. under a vacuum thereby vaporizing a remaining water and the organic compound and solidifying any remaining impurities;

(c) separating a vaporized organic compound and the remaining impurities of the step of (b); and (d) heating a gas separated in the step of (c) to a vapor-phase dehydration reaction temperature of 300 to 500° C.

2. The method of claim 1, wherein a concentration of the organic compound in the fermentation broth is 1-30 wt %.

3. The method of claim 1, wherein a concentration of the organic compound concentrated in the step of (a) is 30-80 wt %.

4. The method of claim 1, wherein the step of (a) comprises directly heating the fermentation broth to a temperature of 38 to 110° C. under a vacuum of 50-750 Torr.

5. The method of claim 1, wherein the concentration of the fermentation broth in the step of (a) is performed using a spiral-type heat exchanger or a multi-stage evaporator, and the vaporization in the step of (b) is performed using a scraped surface heat exchanger.

6. The method of claim 1, further comprising, before the step of (a), preheating the fermentation broth using a spiral-type heat exchanger.

7. The method of claim 1, wherein the step of (c) comprises separating the vaporized organic compound from the impurities in the fermentation broth by a solid/gas separator or an electrostatic precipitator.

8. The method of claim 1, wherein the organic compound has a boiling point higher than that of water.

9. The method of claim 8, wherein the organic compound is selected from the group consisting of 3-hydroxypropionic acid, lactic acid, alcohols having 4 or more carbon atoms, and cyclic alcohols.

10. A method of converting an organic compound by vapor-phase dehydration comprising: heating the organic vapor-phase dehydration feedstock prepared by the method of claim 1 to a reaction temperature; and carrying out a vapor-phase dehydration reaction.

11. The method of claim 10, wherein the reaction temperature ranges from 200° C. to 1000° C.

12. The method of claim 10, further comprising, after the vapor-phase dehydration reaction, a quenching step of cooling a reaction effluent using a solvent to remove remaining water.

13. The method of claim 10, wherein the organic compound is selected from the group consisting of 3-hydroxypropionic acid, lactic acid, alcohols having 4 or more carbon atoms, and cyclic alcohols.

14. A method of converting an organic compound by vapor-phase dehydration comprising: heating the organic vapor-phase dehydration feedstock prepared by the method of claim 6 to a reaction temperature; and carrying out a vapor-phase dehydration reaction.

* * * * *